(12) United States Patent
Al-Assir

(10) Patent No.: US 6,676,664 B1
(45) Date of Patent: Jan. 13, 2004

(54) DEVICE FOR METERING HARDENABLE MASS FOR VERTEBROPLASTIA AND OTHER SIMILAR BONE TREATMENTS

(75) Inventor: Imad Al-Assir, Pozuelo de Alarcon (ES)

(73) Assignee: Grupo Grifols, S.A., Parets Del Valles (Barcelona) (ES)

( * ) Notice: Subject to any disclaimer, the term of this patent is extended or adjusted under 35 U.S.C. 154(b) by 354 days.

(21) Appl. No.: 09/628,873

(22) Filed: Jul. 24, 2000

(30) Foreign Application Priority Data

Aug. 5, 1999 (ES) .................................................. 9901795

(51) Int. Cl.$^7$ .............................................. A61B 17/58
(52) U.S. Cl. ........................................... 606/94; 606/92
(58) Field of Search ............................. 606/59, 60, 62, 606/65, 72, 73, 92, 93, 94; 623/23.63, 23.72, 23.11; 222/390, 527, 388

(56) References Cited

U.S. PATENT DOCUMENTS

| | | | | |
|---|---|---|---|---|
| 4,189,065 A | * | 2/1980 | Herold | 222/46 |
| 4,312,343 A | * | 1/1982 | LeVeen et al. | 128/218 |
| 4,653,489 A | * | 3/1987 | Tronzo | 606/65 |
| 4,969,888 A | | 11/1990 | Scholten et al. | 606/94 |
| 4,986,814 A | * | 1/1991 | Burney et al. | 606/164 |
| 6,086,594 A | * | 7/2000 | Brown | 606/92 |
| 6,217,581 B1 | * | 4/2001 | Tolson | 606/82 |
| 6,241,734 B1 | * | 6/2001 | Scribner et al. | 606/93 |

FOREIGN PATENT DOCUMENTS

| | | | |
|---|---|---|---|
| DE | 34 43 167 A1 | 6/1986 | |
| DE | 3443167 | 6/1986 | A61F/2/46 |
| FR | 2 690 332 | 10/1993 | |
| FR | 2690332 | 10/1993 | A61F/2/46 |
| WO | 95/01809 | 1/1995 | A61L/25/00 |
| WO | WO 95/01809 | 1/1995 | |

* cited by examiner

Primary Examiner—Eduardo C. Robert
Assistant Examiner—David C Comstock
(74) Attorney, Agent, or Firm—Darby & Darby

(57) ABSTRACT

A main metering body has a coupling for a manual pump for filling the hardenable mass for vertebroplastia, permitting its independent filling and its subsequent introduction into the metering body, which is equipped with an end coupling for a high pressure flexible tubular member that can be coupled to the needle for introducing the hardenable mass, capable of being inserted on a long stylet for the initial puncture operation and a short stylet for the second and final puncture to the site where vertebroplastia is to be carried out.

3 Claims, 4 Drawing Sheets

DEVICE FOR METERING HARDENABLE MASS FOR VERTEBROPLASTIA AND OTHER SIMILAR BONE TREATMENTS

The present invention relates to a device for metering hardenable mass for applications of vertebroplastia and other similar bone treatments, achieving significant improvements with respect to the prior art in this field.

As is known, in different pathological states of diverse origin which affect the bone structures (trauma, osteoporosis, bone tumours, bone metastases, osteoarticular implants, etc.), one of the forms of treating, stabilizing and consolidating said structures consists in the injection into their interior of biomaterials having cementing properties which may incorporate drugs having a curative effect.

Access to the interior of the bone structure may be provided by puncture of the bone once exposed in the surgical sphere by means of conventional surgical techniques, or by means of percutaneous puncture, a technique which does not require a surgical incision and in which, instead of this, minimally invasive access through the skin is effected.

Access to the interior of the bone structure may be effected with the operator viewing directly the bone being treated, if the latter has been exposed by means of open surgery. In the case of percutaneous access, the guiding of the puncture needle or needles and their accessories (stylets, fastenings, metallic guides) requires the use of complementary techniques used in medical diagnostics for imaging (fluoroscopy, Computerized Axial Tomography, Magnetic Resonance, etc.) which facilitate the viewing of the path followed by said puncture equipment until it reaches the target in the bone.

The injection of cementing biomaterials is customarily carried out conventionally with standard syringes in which the plunger moves longitudinally along the body of said syringe without there being any type of mechanical connection between the two components. The longitudinal force exerted by the operator is what permits the of the biomaterial, although if this is highly dense or is in a rapid hardening phase, the force to be applied to the plunger needs to be considerable. Owing to the density of the biomaterial to be injected, the conventional syringe is customarily connected directly to the puncture needle, already introduced into the interior of the bone structure. In this way, the distance travelled by the biomaterial between the syringe and its target is shortened, thus reducing as far as possible the force to be generated on the plunger in order for the injection to be effective. The puncture needles customarily used are of large diameter (size or gauge 8, 9 or 10) facilitating the passage of the dense biomaterial through them.

If the biomaterial to be injected is rapid hardening, the procedure for the preparation, loading in the syringe and injection of said material needs to be carried out in a short time (a few minutes). In the contrary case, the hardening of the cement prevents its injection in spite of exerting considerable force on the plunger of the syringe, connecting the syringe directly to the puncture needle, and using large diameter needles.

The aim of the present invention is to improve the methods for injecting hardenable masses in vertebroplastia by facilitating the loading of the biomaterial into the interior of an injector device having special features, making it possible to work with greater injection pressure and to obtain a greater capacity of adjustment thereof, so that the time for which injection of the material is possible is extended.

A further aim of the present invention consists in facilitating access by puncture in the interior of the bone structure by the use of a combination of stylets and needles having special features.

A further aim of the present invention consists in avoiding direct connection between the injection device and the puncture needle in order to avoid excessive exposure of the surgeon to X-rays.

In order to fulfil these aims, the present invention is based on an assembly of two stylets which have the same diameter adapted to the interior of the puncture needle.

The length ratio between the stylets may be variable, as a non-limiting example, from 1:1.5 to 1:3. The long stylet acts as a guide for the needle, which can move along said stylet. The length of the long stylet is such that, once its distal end reaches the outer surface of the bone being treated, the longitudinal portion which remains outside the body of the patient is greater than that introduced into said body.

The short stylet, once introduced completely into the needle, extends beyond the distal end of the latter for a distance of between 1 and 10 mm. That is to say, the length of the needle is slightly less than that of the short stylet.

The present invention also provides for the use of a tube of high pressure flexible plastics material, with connections at both ends adapted to the connections provided on the needle and the device for injecting the biomaterials. The device for injecting biomaterials according to the present invention has a plunger with screw-threaded shaft for exerting high injection pressures, and the body of the device incorporates a lateral entry connection adapted to the connection of conventional syringes, permitting the loading of the biomaterial from a conventional syringe into the body of the injection device.

According to the present invention, the method of introduction of the hardenable mass is characterized by the following operations:

1. Percutaneous Puncture and Access:

Using some diagnostic imaging technology (fluoroscopy, Computerized Axial Tomography, Magnetic Resonance, etc.) for guiding the introduction of the needle within the body of the patient and before initiating the percutaneous puncture, the operator introduces the long stylet completely through the needle.

By manual puncture, the distal end of the stylet is now introduced into the body of the patient. The stylet is advanced while controlling its path with the imaging system selected for the procedure, until the outer surface of the bone being treated is reached. The puncture needle and the proximal portion of the long stylet still remain outside the body of the patient.

The target having been reached with the distal end of the stylet, the puncture needle advances over the latter and is introduced into the inside of the body of the patient until its distal end reaches the distal end of the stylet. The long stylet has been used as described as a guiding element for the needle.

At that moment, the long stylet is substituted by the short stylet, so that the distal end of the latter will project a few millimetres beyond the end of the needle. By means of manual pressure, rotation or percussion, the needle/short stylet assembly is introduced into the interior of the bone to be treated. To inject the biomaterial, the short stylet must be withdrawn.

2. Injection of the Biomaterial:

The body of the injection device must be loaded with the biomaterial as described previously. The high pressure flexible tube will be connected to the body of the device and the rotatable plunger will be advanced until the biomaterial completely occupies the interior of the pressure tube, thus displacing the air which it contained previously.

At that moment the distal end of the pressure tube will be attached to the connection of the needle.

By rotating the plunger of the device in a clockwise direction, the biomaterial will be introduced into the interior of the bone. The system of rotation of the plunger permits controlled, accurate injection, while at the same time allowing the use of different biomaterials even though the latter may be in an advanced state of hardening.

By means of the application of the present invention it is possible to obtain the following advantages compared with the processes known at present.

A. Puncture and Access:

The method proposed is less aggressive or traumatic for the patient. By initially introducing only the stylet, the diameter of the puncture path created is less than that which would be produced if the needle were to be introduced directly. Moreover, in many cases various punctures have to be carried out to reach the target conveniently. With the method proposed, the reorientation of the puncture path is carried out only with the portion of the long stylet introduced into the patient.

The use of the long stylet also makes it possible to keep the operator's hands away from the area subjected to ionizing rays (X-rays), if this technology is used during the procedure. In these circumstances, the irradiation which the hands may receive during the manipulation of the puncture equipment is reduced.

B. Use of the High Pressure Flexible Tube:

This makes it possible to keep the operator's hands away from the irradiated area. Moreover, the movements of the operator's hands are not transmitted to the needle, so that accidental displacements of the latter are avoided.

C. The lateral entry of the device of the invention facilitates the loading of biomaterials into its interior. Using a conventional syringe, it is possible to transfer the biomaterial to the device of the invention in a few seconds.

D. The rotatable plunger, with screw-threaded shaft, allows the operator to carry out the injection of the biomaterial with total accuracy. Even if the biomaterial is in an advanced state of hardening, the injection is possible. Once the desired quantity of biomaterial is injected, the injection is stopped easily by applying anticlockwise rotation to the plunger (negative pressure).

For greater understanding thereof, drawings of a preferred embodiment of the present invention are appended by way of non-limiting example.

Figure 1:
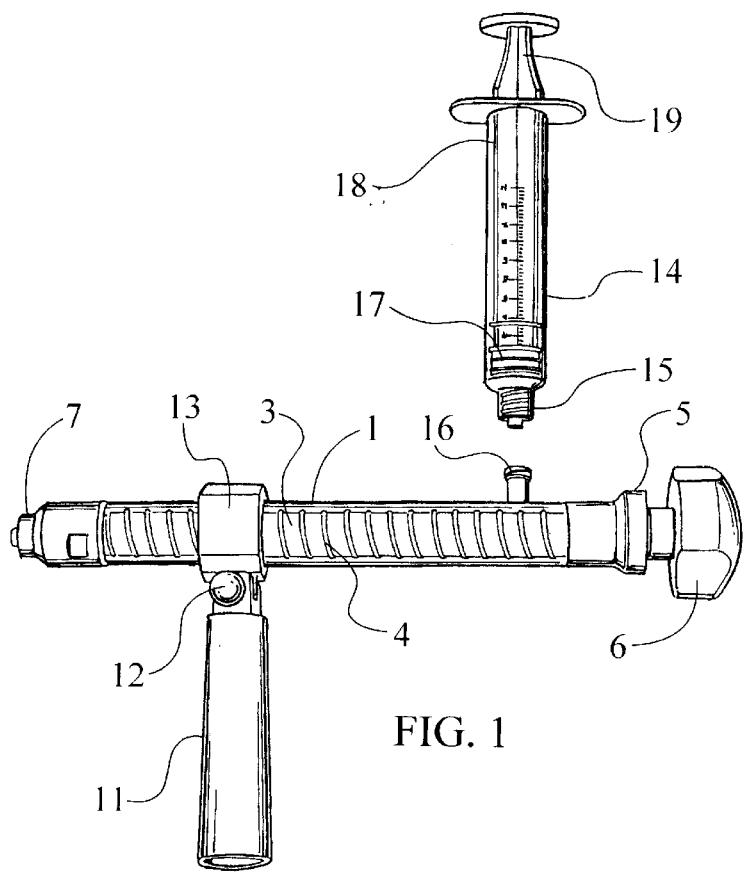
FIG. 1 is a view in elevation of a vertebroplastia injector device according to the present invention.
Figures 2, 3, 4:
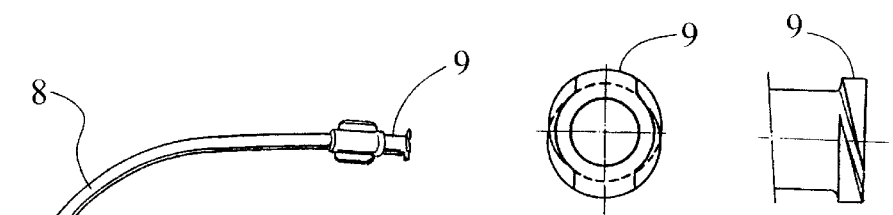
FIG. 2 is a plan view of the high pressure tubular member.
FIGS. 3 and 4 are respective views in front elevation and side elevation of one of the terminals of the tubular member in FIG. 2.
Figure 5:
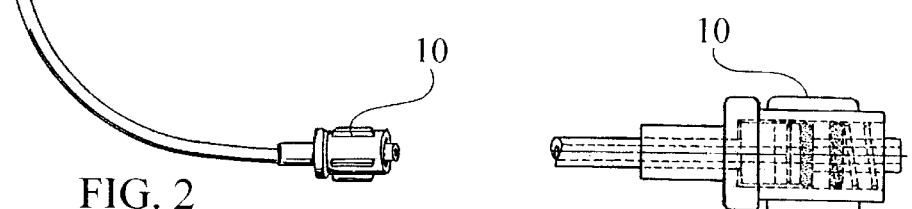
FIG. 5 shows a detail of the second terminal of said tubular member.

As shown in the drawings, the vertebroplastia device of the present invention comprises a main metering body I with an internally movable plunger 2 integral with the actuating rod 3, which is provided with a screw-thread 4 on its outer surface which combines with a complementary screw-thread of the entry region 5 of the body 1 so that the knob or control 6 coupled to the rod 3 can be rotated manually in one direction or the other, advancing or withdrawing the plunger 2, increasing or reducing the free volume of the body 1, so that the freeing of the interior volume of said body is obtained for the purpose of loading the latter, or the gradual compression of the hardenable mass which is inside it, in order to cause it to emerge through the terminal end 7 of said body, to which is coupled a tubular member or extension 8 provided with quick-fit terminals 9 and 10, to permit the subsequent placing of the stylets and the needle as will be explained.

A manual handle 11 is coupled in an articulated manner, by means of the articulation 12 and a retaining device in the form of a small ring 13, to the body 1 to facilitate its manipulation.

For the filling of the metering body, the present invention provides a lateral filling pump 14 constituted by a cylinder with lower coupling of the quick-fit type 15 which can be coupled to a lateral mouthpiece 16 of the body 1 and which has internally an assembly of plunger 17 and rod 18, integral with the outer handle 19. Said pump may be constituted by a conventional syringe.

The mouthpiece 16 is located in a position close to the end 5 of the main body so that when the plunger 2 is in the position of maximum internal free volume, the mouthpiece 16 communicates with the internal volume so that, once the hardenable mass is transferred to the body 1, the movement of the plunger by clockwise rotation of the assembly 34 closes the direct communication between the mouthpiece 16 and the internal volume, now full, of the body 1, thus preventing reflux of the hardenable material towards the pump 14, and further permitting the disconnection of the latter immediately for the purpose of manoeuvrability.

This arrangement of components allows the regular and uniform filling of the body 1 on proceeding with the prior filling of the manual pump 14 and then coupling it to the mouthpiece 16 so that, by actuating the terminal 19, the charge of hardenable mass is transferred towards the inside of the main body 1 and subsequently, on rotating the knob 6, the plunger 2 will bring about the gradual displacement of the mass, causing it to emerge through the terminal 7 and tubular member 8 capable of receiving high pressures.

Figure 6:
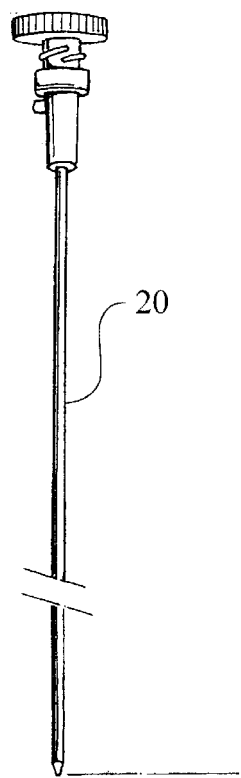
FIGS. 6 and 7 show two puncture stylets, respectively short and long.
Figure 7:
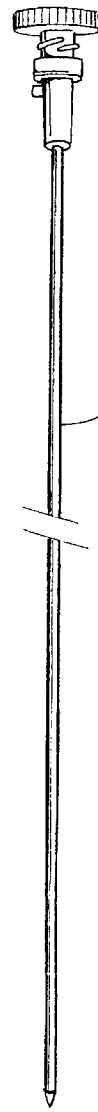
Figure 8:
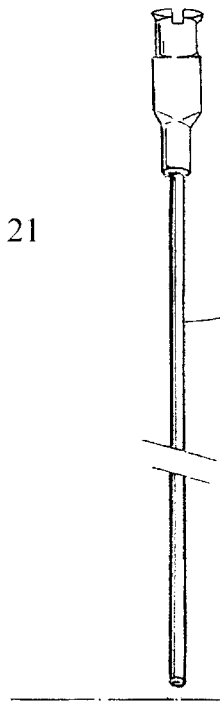
FIG. 8 is a view of the puncture needle.
Figure 9:
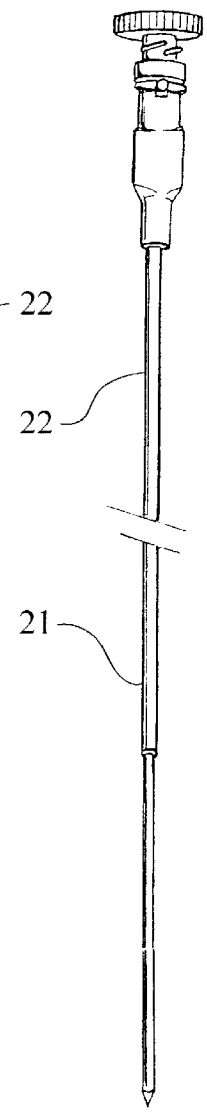
FIG. 9 shows the placing of the long stylet within the needle.
Figure 10:
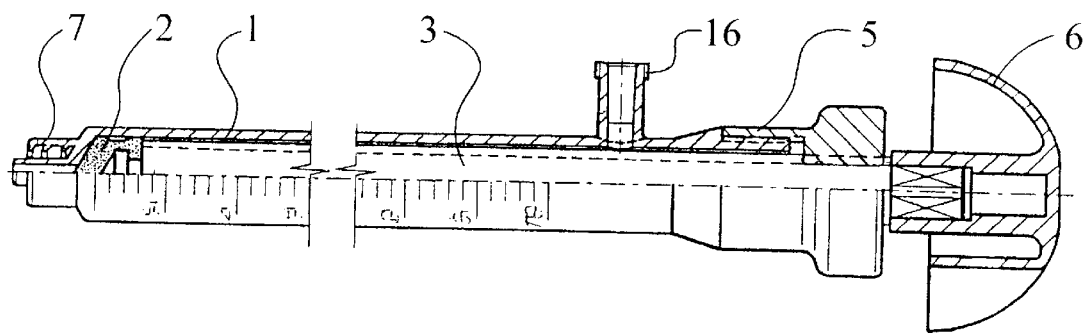
FIG. 10 is a view in side elevation, with partial section, of the metering syringe of the device.
Figure 11:
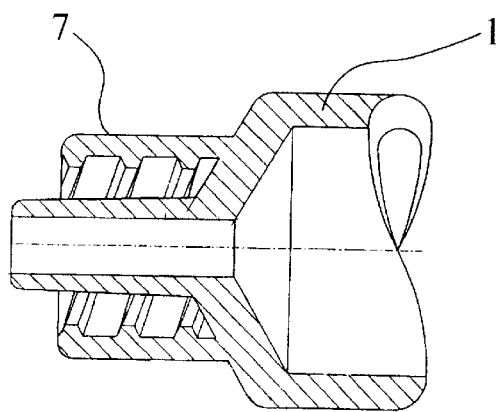
FIG. 11 shows a detail in section of the terminal of the syringe in FIG. 10.
Figure 12:
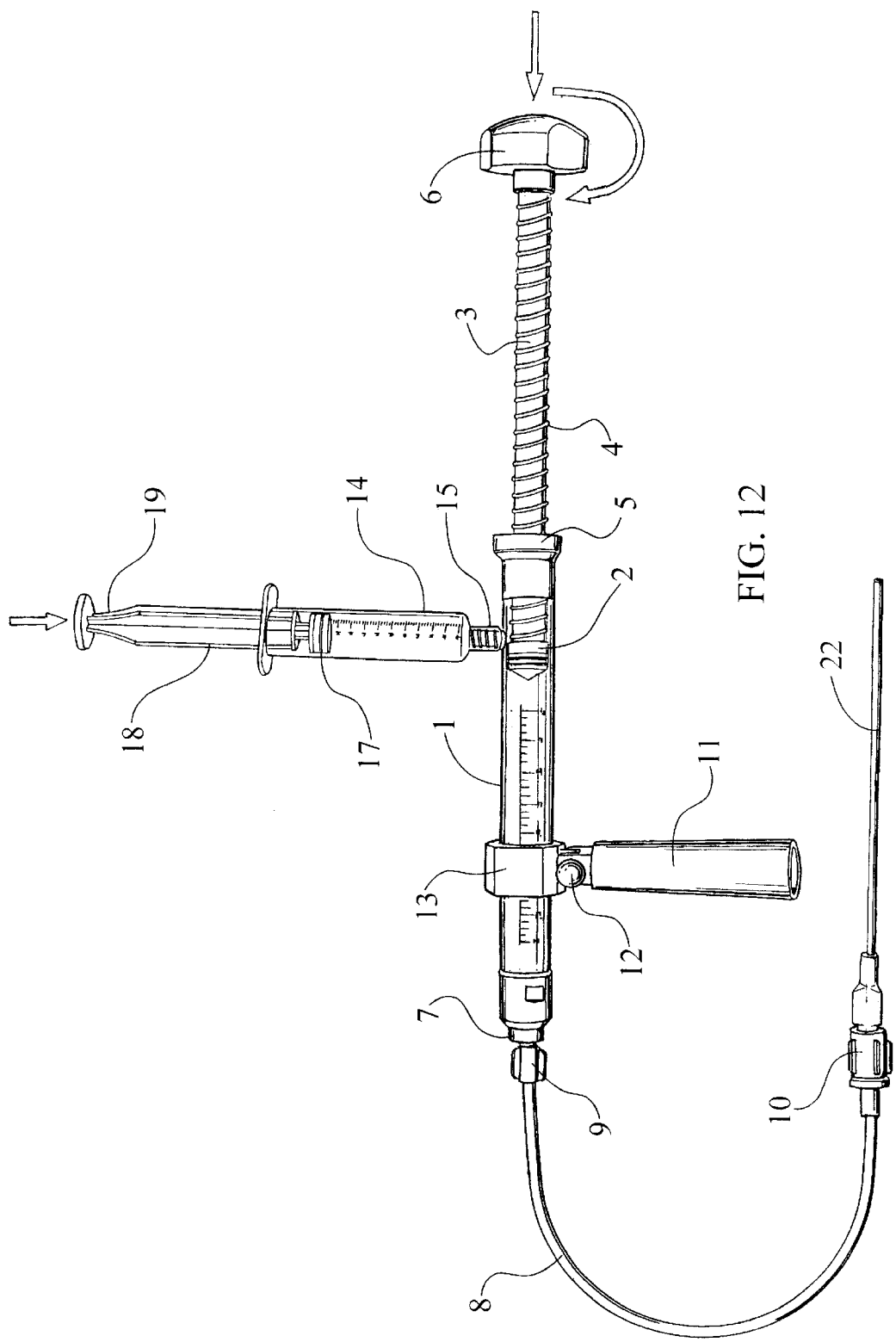
FIG. 12 is a view of the vertebroplastia device of the present invention.

The assembly of stylets and needle which form part of the present device have been shown in FIGS. 6, 7, and 8. First of all, the device has two stylets of different length 20 and 21. The long stylet has a length greater than that of the short stylet in a variable ratio which, as a non-limiting indication, may be between 30 and 50%, having the purpose of effecting the first puncture so that its end remains located in proximity to the site at which it is desired to carry out vertebroplasty, for which the assistance of X-ray screens or the like of customary type in this art will be employed. After the first operation indicated, for which the hollow needle 22 will have previously been introduced, on the stylet 21, forming the assembly shown in FIG. 9, the entry of the needle 22 may be brought about until it is introduced into the site where vertebroplasty is to be carried out, in which position the long stylet 21 will be extracted and will be substituted by the short stylet 20, which will make it possible to carry out more intense penetration towards the site where the hardenable mass is to be injected. In these circumstances, the short stylet will be extracted and the needle will be connected to the metering body of the device for injecting hardenable mass in order to effect the progressive entry of the hardenable mass at the site provided for vertebroplasty.

By means of the device of the present invention it is possible to improve significantly all the functions necessary for carrying out vertebroplasty similar bone treatments, from the loading of the metering body of the pressure propulsion cylinder, expulsion of the mass, even in a certain phase of hardening, the possibility that the tubular member coupled to the metering body can resist high pressures, and great facility in the process of puncture and subsequent introduction of the hardenable mass. The mass to be injected may vary, being of the cement or paste-like substance or other type.

Moreover, owing to the arrangement of the tubular member capable of functioning at high pressure, the surgeon's hands can remain substantially separated from the direct site of the intervention, thus avoiding excessive exposure to the radiation of the X-ray apparatus used for locating the site of the operation.

What is claimed is:

1. A device for metering a hardenable mass for vertebroplasty comprising a main metering body with a screw-threaded shaft coupled to a propulsion plunger, wherein the main metering body has a coupling for a manual pump which is independently filled with the hardenable mass and subsequently introduces the hardenable mass into the metering body, and wherein the metering body is also equipped with an end coupling coupled to a high pressure flexible tubular member coupled to a needle for introducing the hardenable mass into a patient, the needle being inserted on a long stylet for an initial puncture and on a short stylet for a second and final puncture to a site where vertebroplasty is to be carried out.

2. The device of claim 1, wherein the stylets have the same diameter, and the length of the long stylet is preferably 30 to 50% longer than that of the short stylet.

3. A method for vertebroplasty comprising the steps of:
providing a device for metering a hardenable mass for vertebroplasty comprising a main metering body with a screw-threaded shaft coupled to a propulsion plunger, wherein the main metering body has a coupling for a manual pump which is independently filled with the hardenable mass and subsequently introduces the hardenable mass into the metering body, and wherein the metering body is also equipped with an end coupling for a high pressure flexible tubular member that can be coupled to a needle for introducing the hardenable mass into a patient the needle being insertable on a long stylet for an initial puncture and on a short sytlet for a second and final puncture to a site where vertebroplasty is to be carried out;

puncturing the body of a patient with the long stylet until the distal end thereof is near the site at which the hardenable mass is to be injected;

sliding the needle, which was previously inserted on the long stylet, so as to penetrate close to the vertebroplasty site;

substituting the long stylet with the short stylet for the final puncture to the vertebroplasty site;

extracting the short stylet with the needle remaining in the vertebroplasty site;

connecting to the end of the metering body a high pressure tubular member, the metering body having been previously filled by means of an auxiliary pump; and injecting the hardenable mass by via the plunger of said metering body.

\* \* \* \* \*

UNITED STATES PATENT AND TRADEMARK OFFICE
CERTIFICATE OF CORRECTION

| | | |
|---|---|---|
| PATENT NO. | : 6,676,664 B1 | Page 1 of 1 |
| APPLICATION NO. | : 09/628873 | |
| DATED | : January 13, 2004 | |
| INVENTOR(S) | : Imad Y. Al-Assir | |

It is certified that error appears in the above-identified patent and that said Letters Patent is hereby corrected as shown below:

In the Assignee:

Delete "Grupo Grifols, S.A." and substitute -- Probitas Pharma, S.A. --

Signed and Sealed this

Twenty-ninth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,676,664 B1
APPLICATION NO. : 09/628873
DATED : January 13, 2004
INVENTOR(S) : Imad Y. Al-Assir It is certified that error appears in the above-identified patent and that said Letters Patent is hereby corrected as shown below:

On Title Page Item -75-

In the Inventor's name:

Delete "Imad Al-Assir" and substitute -- Imad Youssef Al-Assir --.

Signed and Sealed this

Eighth Day of May, 2007

JON W. DUDAS
*Director of the United States Patent and Trademark Office*